US012496388B2

(12) United States Patent
Hamao et al.

(10) Patent No.: US 12,496,388 B2
(45) Date of Patent: Dec. 16, 2025

(54) PHOTODYNAMIC THERAPY DEVICE COMPRISING COOLING WATER CIRCULATION UNIT FOR BLOOD

(71) Applicant: OTSUKA ELECTRONICS CO., LTD., Hirakata (JP)

(72) Inventors: Tamotsu Hamao, Hirakata (JP); Akira Tanaka, Hirakata (JP); Shinpei Kajiwara, Hirakata (JP)

(73) Assignee: OTSUKA ELECTRONICS CO., LTD., Hirakata (JP)

( * ) Notice: Subject to any disclaimer, the term of this patent is extended or adjusted under 35 U.S.C. 154(b) by 335 days.

(21) Appl. No.: 18/031,533

(22) PCT Filed: Oct. 14, 2020

(86) PCT No.: PCT/JP2020/038764

§ 371 (c)(1),
(2) Date: Apr. 12, 2023

(87) PCT Pub. No.: WO2022/079827

PCT Pub. Date: Apr. 21, 2022

(65) Prior Publication Data

US 2023/0372597 A1 Nov. 23, 2023

(51) Int. Cl.
*A61M 1/36* (2006.01)
*A61N 5/06* (2006.01)

(52) U.S. Cl.
CPC ........ *A61M 1/3683* (2014.02); *A61M 1/3623* (2022.05); *A61M 2205/3368* (2013.01); *A61M 2205/3606* (2013.01); *A61N 5/062* (2013.01)

(58) Field of Classification Search
CPC .............. A61M 1/3683; A61M 1/3623; A61M 2205/3368; A61M 2205/3606; A61N 5/062
See application file for complete search history.

(56) References Cited

U.S. PATENT DOCUMENTS 4,573,962 A 3/1986 Troutner
5,263,925 A 11/1993 Gilmore, Jr. et al.
(Continued)

FOREIGN PATENT DOCUMENTS

CN 104548233 A 4/2015
CN 106880881 A 6/2017
(Continued)

OTHER PUBLICATIONS

International Search Report dated Dec. 15, 2020 in Application No. PCT/JP2020/038764.
(Continued)

*Primary Examiner* — Susan S Su
(74) *Attorney, Agent, or Firm* — Sughrue Mion, PLLC

(57) ABSTRACT

The photodynamic therapy device of the present disclosure is a photodynamic therapy device that irradiates light from a light source onto blood that has been taken out of a patient's body and is flowing in the blood tube, the blood having absorbed a photoreactive agent, to destroy an undesirable component in the blood or affect the component. The photodynamic therapy device includes the irradiation unit that includes a light source and irradiates the blood in the blood tube with light, and the circuit cooling block that cools the blood in the blood tube. The circuit cooling block is connected to the pump that circulates cooling water in the circuit cooling block, the reservoir tank, and the cooling unit that cools water by the water flow path for flowing the cooling water.

5 Claims, 15 Drawing Sheets

(56) References Cited

U.S. PATENT DOCUMENTS

| | | | | |
|---|---|---|---|---|
| 5,290,221 | A | 3/1994 | Wolf, Jr. et al. | |
| 5,702,432 | A * | 12/1997 | Chen | A61N 5/062 604/21 |
| 2009/0156976 | A1 | 6/2009 | Korbling et al. | |
| 2011/0021966 | A1 * | 1/2011 | Leonard | A61M 37/00 210/748.14 |
| 2015/0150715 | A1 | 6/2015 | Svitek et al. | |
| 2019/0099543 | A1 | 4/2019 | Sasaki | |
| 2019/0209718 | A1 | 7/2019 | Church et al. | |
| 2019/0374701 | A1 * | 12/2019 | Lahmann | A61M 1/3672 |
| 2022/0133976 | A1 | 5/2022 | Tanaka et al. | |

FOREIGN PATENT DOCUMENTS

| | | | |
|---|---|---|---|
| CN | 207674816 | U | 7/2018 |
| CN | 109646808 | A | 4/2019 |
| CN | 110101928 | A | 8/2019 |
| JP | 2000-093449 | A | 4/2000 |
| JP | 2005-518837 | A | 6/2005 |
| JP | 2013-517093 | A | 5/2013 |
| KR | 10-2019-0002231 | A | 1/2019 |
| WO | 83/00088 | A1 | 1/1983 |
| WO | 03/071999 | A1 | 9/2003 |
| WO | 2011/090885 | A2 | 7/2011 |
| WO | 2017/164202 | A1 | 8/2017 |
| WO | 2019/086631 | A1 | 5/2019 |
| WO | 2020/174589 | A1 | 9/2020 |

OTHER PUBLICATIONS

International Preliminary Report on Patentability dated Apr. 27, 2023 with a Translation of the Written Opinion of the International Searching Authority in Application No. PCT/JP2020/038764.

Extended European Search Report issued Mar. 18, 2024 in European Application No. 20957656.0.

* cited by examiner

PHOTODYNAMIC THERAPY DEVICE COMPRISING COOLING WATER CIRCULATION UNIT FOR BLOOD

TECHNICAL FIELD

The present disclosure relates to a photodynamic therapy device including a cooling water circulation unit for blood.

BACKGROUND ART

In photodynamic therapy (PDT), blood having absorbed a photoreactive agent having a characteristic light absorption band is once taken out of a patient's body and irradiated with a light beam corresponding to the characteristic light absorption band, thereby destroying or affecting undesirable components in the blood. For example, an LED is used as a light source of a light beam which is irradiation light.

By the way, when the blood taken out of the patient's body is irradiated with the light beam by the LED at the time of the PDT treatment described above, the blood generates heat and the temperature rises. An increase in the temperature of the blood may place a burden on the patient's body to which the blood is returned. Furthermore, an increase in temperature adversely affects the blood itself.

PRIOR ART DOCUMENT

Patent Document

Patent Document 1: WO 2017/164202 A

SUMMARY OF THE INVENTION

Problems to be Solved by the Invention

The present disclosure provides a photodynamic therapy device that suppresses an increase in blood temperature in PDT.

Means for Solving the Problems

The photodynamic therapy device of the present disclosure is a photodynamic therapy device that irradiates light from a light source onto blood that has been taken out of a patient's body and is flowing in a blood tube, the blood having absorbed a photoreactive agent, to destroy an undesirable component in the blood or to affect the component. Such a photodynamic therapy device includes:

- an irradiation unit that includes the light source and irradiates the blood in the blood tube with light; and
- a circuit cooling block that cools the blood in the blood tube.

The circuit cooling block is connected to a pump that circulates cooling water in the circuit cooling block, a reservoir tank, and a cooling unit that cools water, by a water flow path that flows the cooling water.

Effects of the Invention

In the photodynamic therapy device of the present disclosure, a temperature rise caused by the heat generation of the blood due to the absorption of the irradiation light is suppressed.

MODES FOR CARRYING OUT THE INVENTION

Figure 1A:
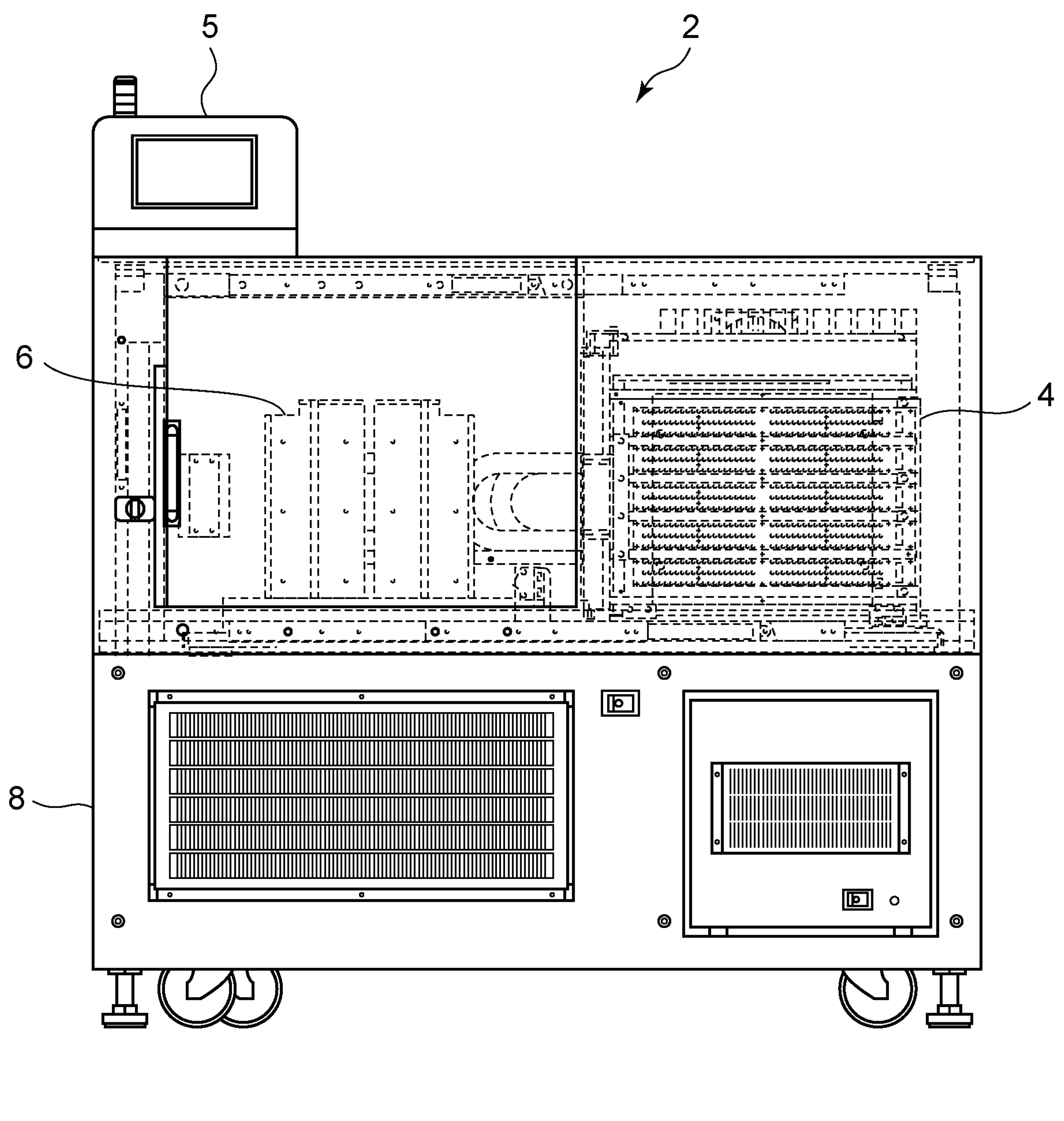
FIG. 1A is a front view of a photodynamic therapy device according to an embodiment of the present disclosure.

In the following, an embodiment will be described in detail with reference to the drawings as appropriate. However, unnecessarily detailed descriptions will be omitted in some cases. For example, detailed descriptions of already well-known matters and repetition of descriptions of substantially the same configuration will be omitted in some cases. This is to prevent the following description from being unnecessary redundant and to facilitate those skilled in the art to understand the present disclosure.

Note that the inventors provide the accompanying drawings and the following description in order for those skilled in the art to fully understand the present disclosure, and does not intend to limit the subject matter described in the claims by the accompanying drawings and the following description.

1. Background to Present Disclosure

Photodynamic therapy (PDT) is a treatment method in which a photosensitizer or a precursor thereof is administered, the photosensitizer or the precursor thereof is accumulated in an affected area such as a tumor tissue, a new blood vessel, or a skin surface, a light beam corresponding to an absorption band wavelength of the photosensitizer is irradiated as excitation light, and a cytocidal effect of active oxygen species including singlet oxygen generated by the excitation is utilized.

Taking an example in which a patient is a hematologic cancer patient and has tumor cells, in photodynamic therapy, first 5-aminolevulinic acid (5-ALA) having oral absorbability is administered to the patient. Then, in the process of biosynthesis of heme in intracellular mitochondria, aminolevulinic acid is metabolized to protoporphyrin IX (PpIX) which is a photosensitizer. Since protoporphyrin IX has a property of accumulating in mitochondria in a tumor cell specific manner, protoporphyrin IX accumulates in tumor cells of a patient.

Subsequently, in the photodynamic therapy, a patient's circulatory organ is connected to an irradiation device for the photodynamic therapy via a blood circuit for flowing blood. The blood of the patient contains tumor cells in which the protoporphyrin IX is accumulated, and the blood flows into the irradiation device through the blood circuit by the action of a circulation pump connected to the blood circuit for flowing blood. In the irradiation device, when light in a wavelength range (for example, in the vicinity of 410 nm and in the vicinity of 500 to 650 nm) where protoporphyrin IX can absorb is irradiated, the protoporphyrin IX contained in the blood becomes in an excited singlet state. The protoporphyrin IX returns from the excited singlet state to the ground state through an excited triplet state. Oxygen that has absorbed the energy at that time becomes singlet oxygen, and can destroy or affect tumor cells in the blood. The blood that has been irradiated with light is returned to the patient's circulatory organ by the action of the circulation pump via the blood circuit for flowing blood.

The blood circuit is connected to a translucent blood tube formed of a predetermined resin in the irradiation device. The blood tube through which blood flows inside is irradiated with a light beam corresponding to an absorption band wavelength of protoporphyrin IX, which is a photosensitive substance, by an LED, which is a light source, for example. At this time, the inventors have noticed that the blood may generate heat due to absorption of the irradiation light, and a temperature of the blood may rise. In particular, the illuminance of the light source must be correspondingly increased in order to obtain a sufficient effect for the photodynamic therapy at a treatment time (for example, 3 hours) that does not significantly affect the patient's physical strength. In that case, according to trial calculation and trial by the inventors, the temperature of the blood may reach 60° C. An increase in the temperature of the blood imposes a burden of a high temperature on the patient's body to which the blood is returned. Moreover, the increase in temperature adversely affects the blood itself.

Note that the inventors have found that it is desirable that the temperature of the blood that can be increased by the irradiation device is 40° C. or lower at most by a large number of trials and trial calculations.

The present disclosure overcomes these problems, and provides a photodynamic therapy device that suppresses a temperature rise of blood due to irradiation light in the photodynamic therapy.

2. Embodiment

Hereinafter, preferred embodiments of the present disclosure will be described with reference to the accompanying drawings.

2.1. Configuration of Photodynamic Therapy Device

First, a configuration of a photodynamic therapy device according to an embodiment will be described.

2.1.1. Schematic Configuration of Photodynamic Therapy Device

Figure 1B:
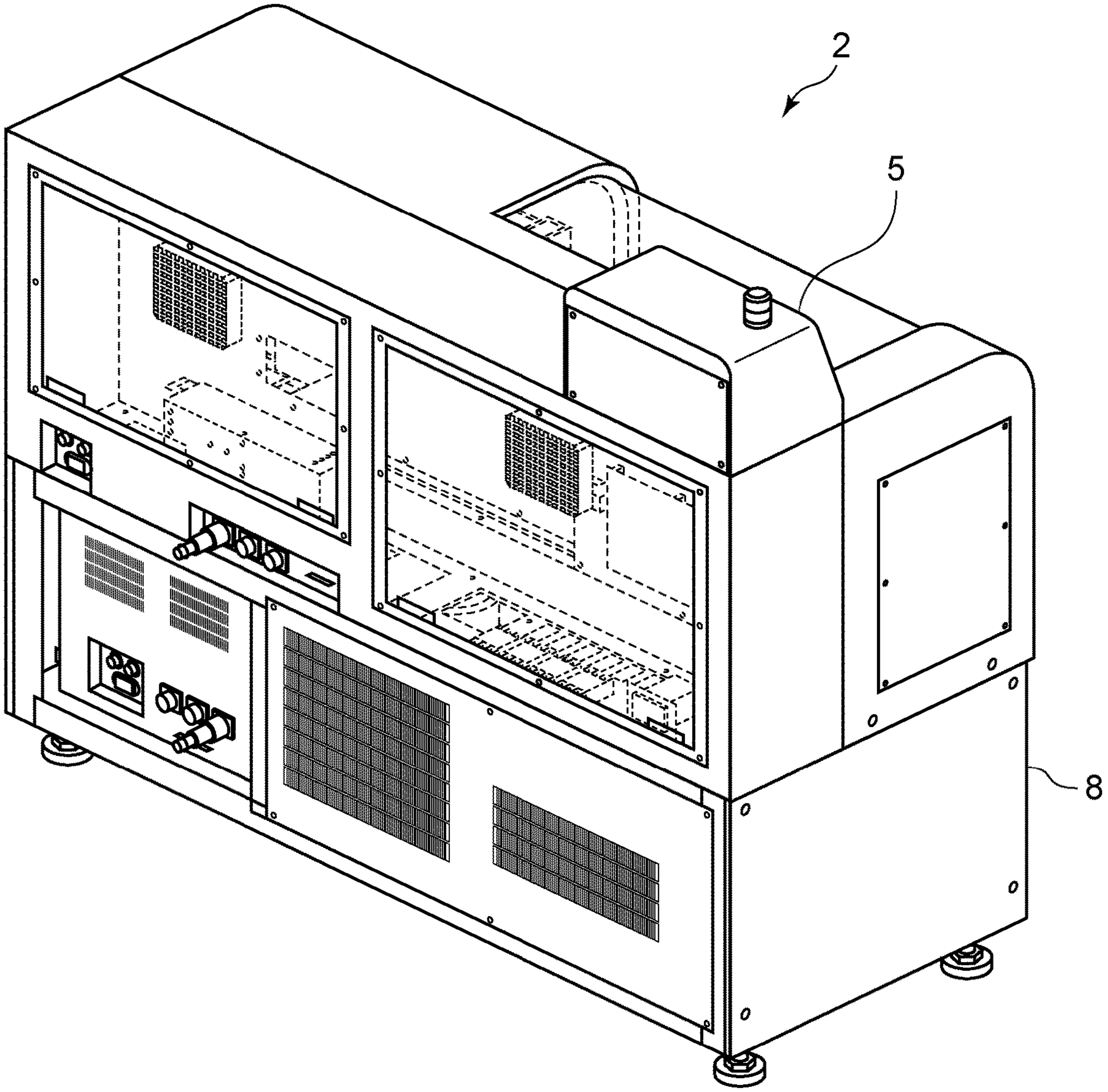
FIG. 1B is a rear perspective view of the photodynamic therapy device according to the embodiment.

FIG. 1A is a front view of a photodynamic therapy device 2 according to the embodiment. FIG. 1B is a rear perspective view of the photodynamic therapy device 2 according to the same embodiment.

As illustrated in FIG. 1A, the photodynamic therapy device 2 includes a circuit cooling block 6 and an irradiation unit 4.

The circuit cooling block 6 is formed of a predetermined material, and as will be described later, is inserted into a circuit holder 22 (See FIGS. 3A, 3B, etc.) including a blood tube 34 (See FIGS. 5 and 9.) connected to a blood circuit for flowing blood (that is, forming part of the blood circuit), and comes into contact with an inner surface of the circuit holder 22 to cool the blood tube 34 and the blood. The material forming the circuit cooling block 6 is desirably a metal having high thermal conductivity, for example, aluminum. The irradiation unit 4 irradiates the blood tube and the blood in the circuit holder 22 with a light beam corresponding to a characteristic light absorption band. The irradiation unit 4 includes, inside the irradiation unit 4, a light source (not illustrated) including a large number of light emitting elements (for example, LEDs) and a light detection unit (not illustrated) including light detection elements. A large number of the light emitting elements constituting the light source are arranged, for example, in a matrix inside a pair of left and right wider side surface portions (See FIGS. 2A and 2B.) facing each other of the irradiation unit 4. The light detection unit is disposed, for example, inside an upper surface and inside a bottom surface of the irradiation unit 4.

The photodynamic therapy device 2 illustrated in FIG. 1A is further provided with a lower casing 8. The lower casing 8 houses a cooling unit 16, a first valve 14*a* and a second valve 14*b*, a reservoir tank 18, and a pump 20 that constitute a cooling water circulation unit described later with reference to FIGS. 8 and 9.

Furthermore, in the photodynamic therapy device 2 illustrated in FIGS. 1A and 1B, an opening/closing operation of the valves to be described later and the like are performed through an operation on an operation unit 5 provided in an upper portion.

Figure 2A:
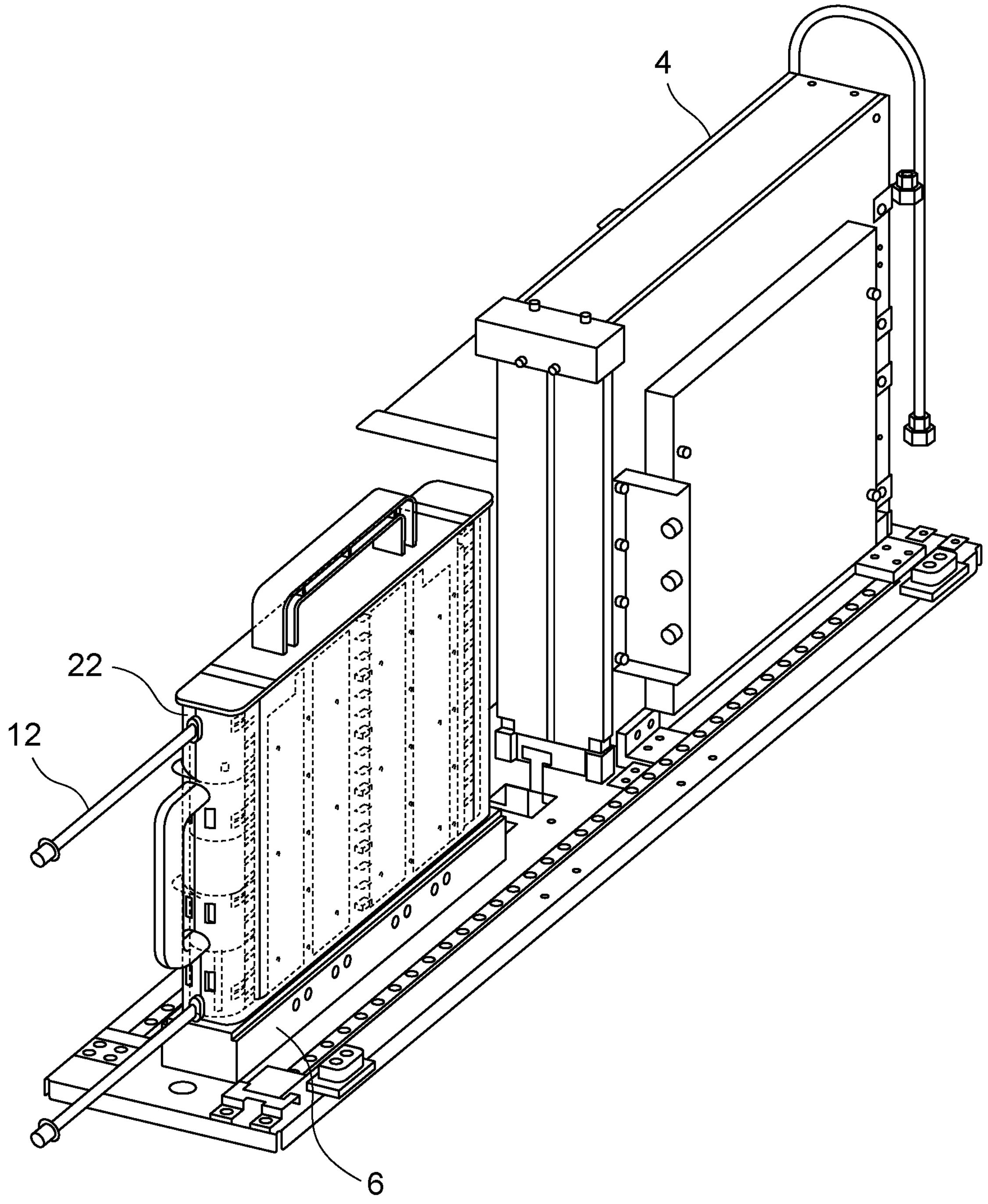
FIG. 2A is a perspective view of a circuit holder, a circuit cooling block, and an irradiation unit in the photodynamic therapy device according to the embodiment. An arrangement of the irradiation unit, the circuit holder, and the circuit cooling block in the drawing is at the time of monitoring an amount of light.

2.1.2. Configuration of Circuit Holder, Circuit Cooling Block, and Irradiation Unit FIG. 2A is a perspective view of the circuit holder 22, the circuit cooling block 6, and the irradiation unit 4 in the photodynamic therapy device 2 according to the embodiment. As also illustrated in FIG. 2A, the circuit cooling block 6 is inserted inside the circuit holder 22. The irradiation unit 4 is configured to be relatively movable with respect to the circuit holder 22 and the circuit cooling block 6. Note that, in the embodiment illustrated in FIGS. 2A and 2B, the irradiation unit 4 can move with respect to the fixed circuit cooling block 6. In a state where the circuit holder 22 and the circuit cooling block 6 are separated from the irradiation unit 4, the irradiation unit 4 monitors a light amount using the light source and the light detection unit.

Figure 2B:
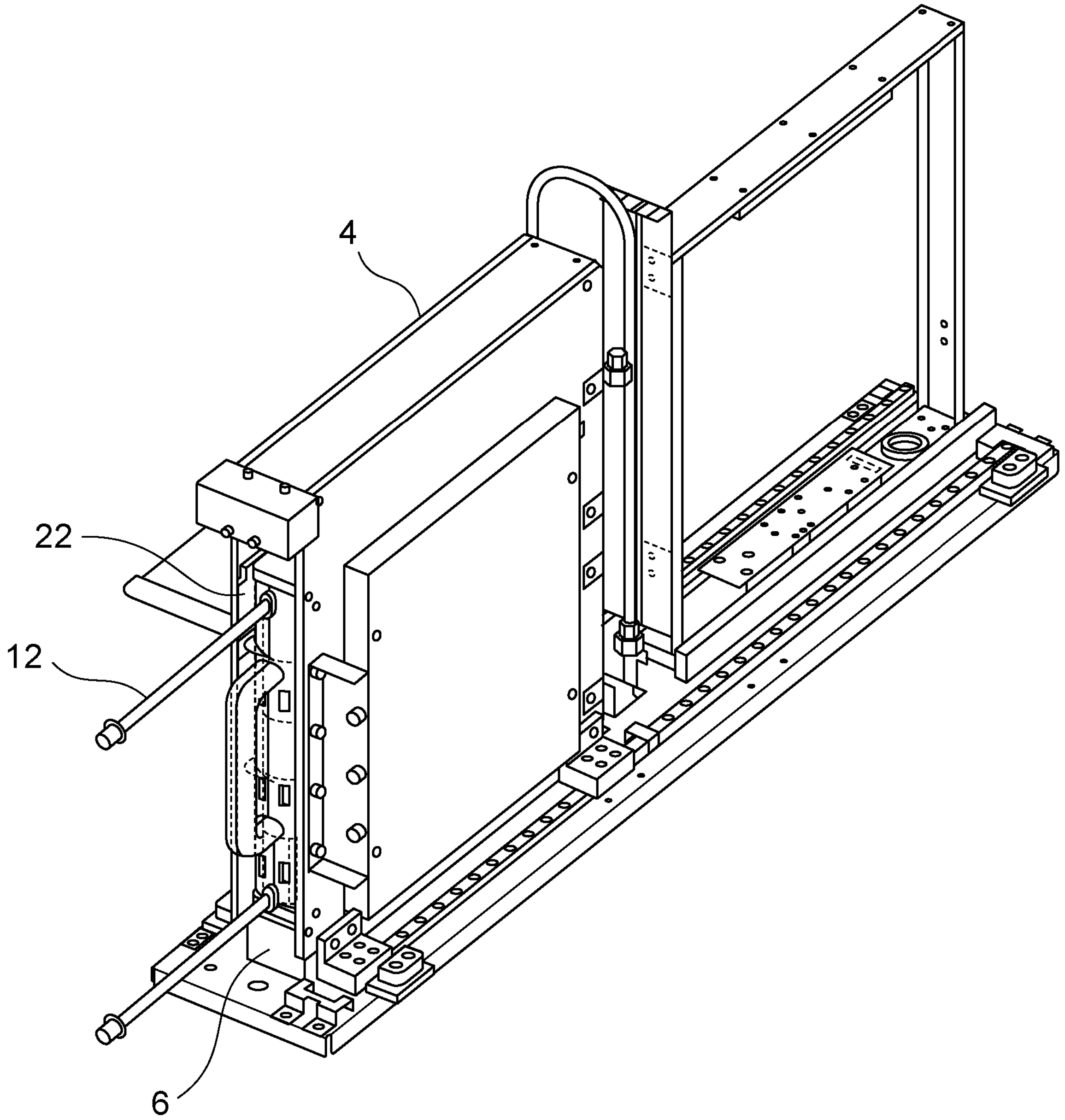
FIG. 2B is a perspective view of the circuit holder, the circuit cooling block, and the irradiation unit in the photodynamic therapy device according to the embodiment. An arrangement of the irradiation unit, the circuit holder, and the circuit cooling block in the drawing is at the time of treatment.

FIG. 2B is also a perspective view of the circuit holder 22, the circuit cooling block 6, and the irradiation unit 4. The circuit holder 22 and the circuit cooling block 6 are accommodated inside the irradiation unit 4 by movement of the irradiation unit 4 relative to the circuit holder 22 and the circuit cooling block 6. At this time, the pair of left and right light sources inside the irradiation unit 4 are arranged to face a pair of side surfaces of the circuit holder 22. The pair of left and right light sources of the irradiation unit 4 is arranged to face the pair of side surfaces of the circuit holder 22, and treatment by light irradiation of the irradiation unit 4 is performed.

2.1.3. Configuration of Circuit Holder and Circuit Cooling Block

Figure 3A:
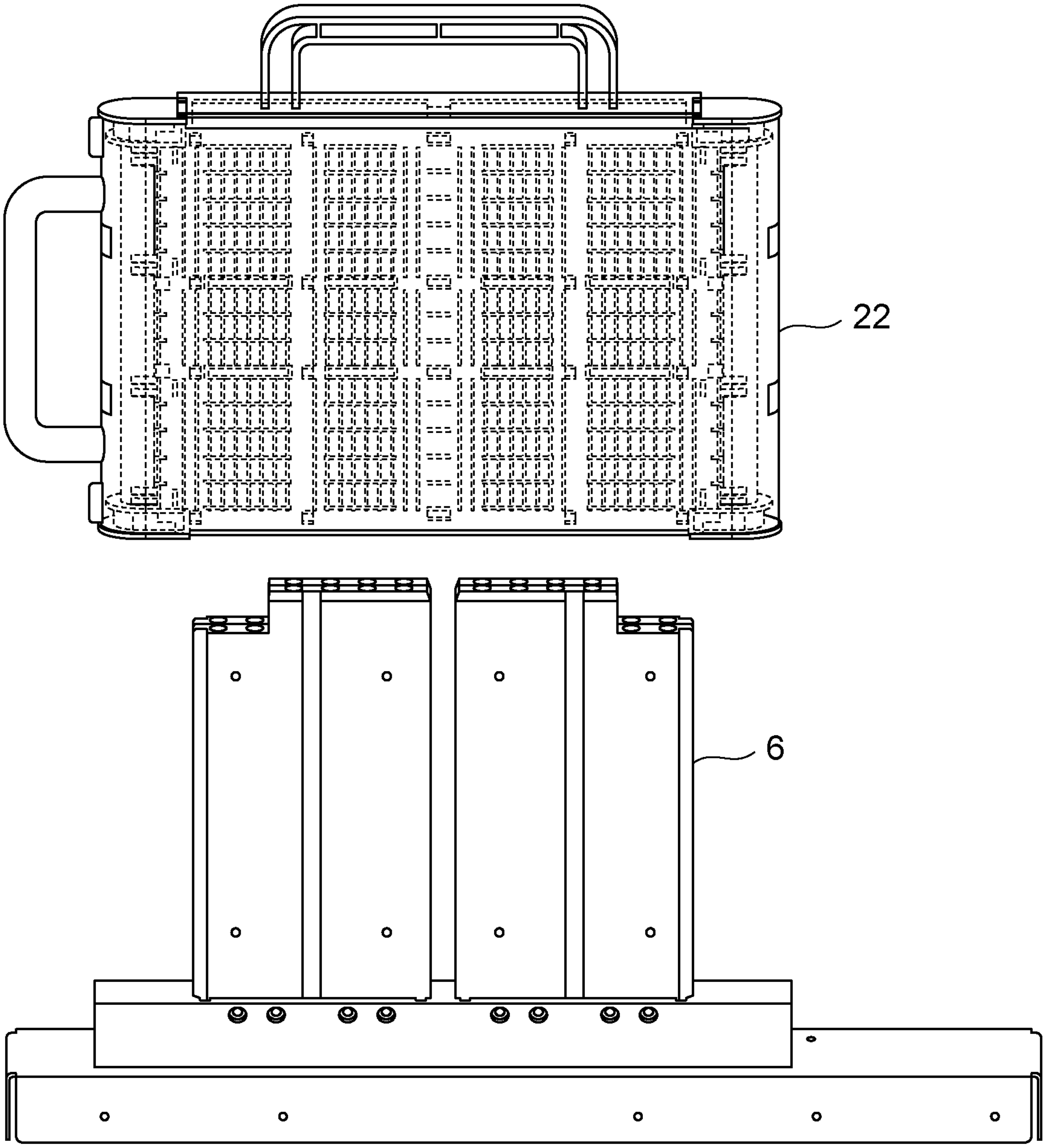
FIG. 3A is a substantially front perspective view of the circuit holder and the circuit cooling block in the photodynamic therapy device according to the embodiment.
Figure 3B:
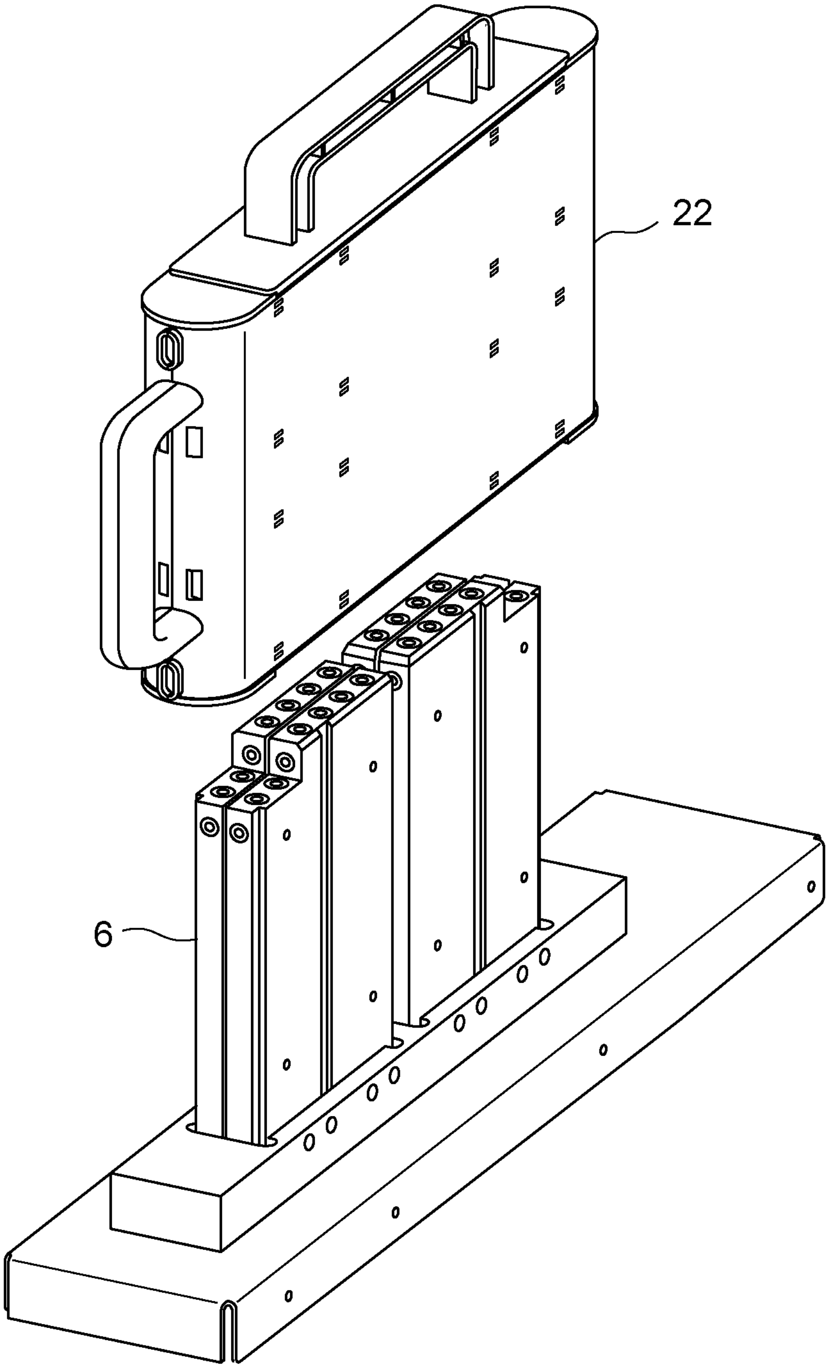
FIG. 3B is a perspective view of the circuit holder and the circuit cooling block in the photodynamic therapy device according to the embodiment.

FIG. 3A is a substantially front perspective view of the circuit holder 22 and the circuit cooling block 6 in a separated state in the photodynamic therapy device 2 according to the embodiment. FIG. 3B is also a perspective view of the circuit holder 22 and the circuit cooling block 6 in a separated state in the photodynamic therapy device 2 according to the embodiment.

Figure 4A:
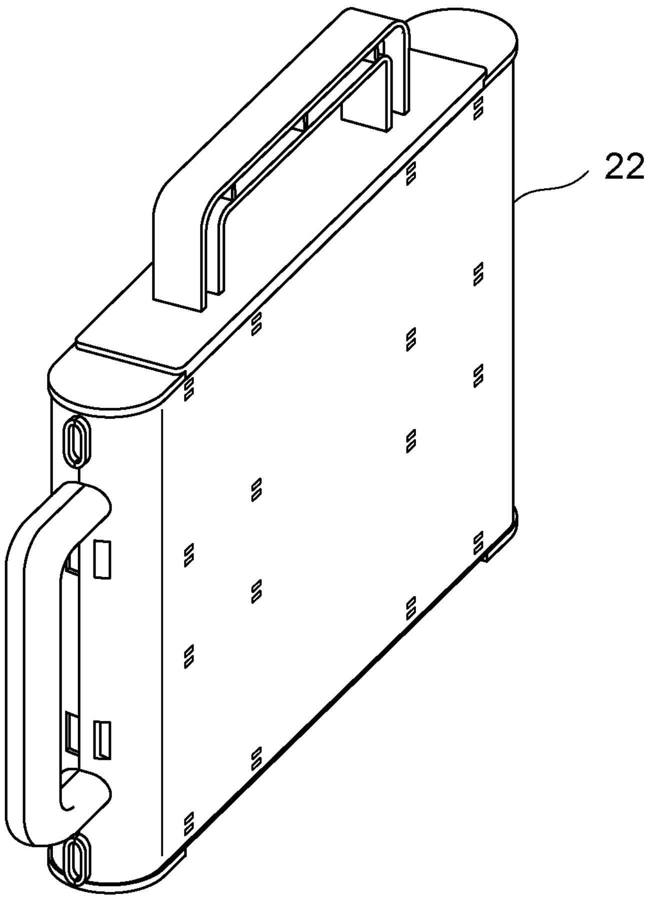
FIG. 4A is a perspective view of the circuit holder in the photodynamic therapy device according to the embodiment.
Figure 4B:
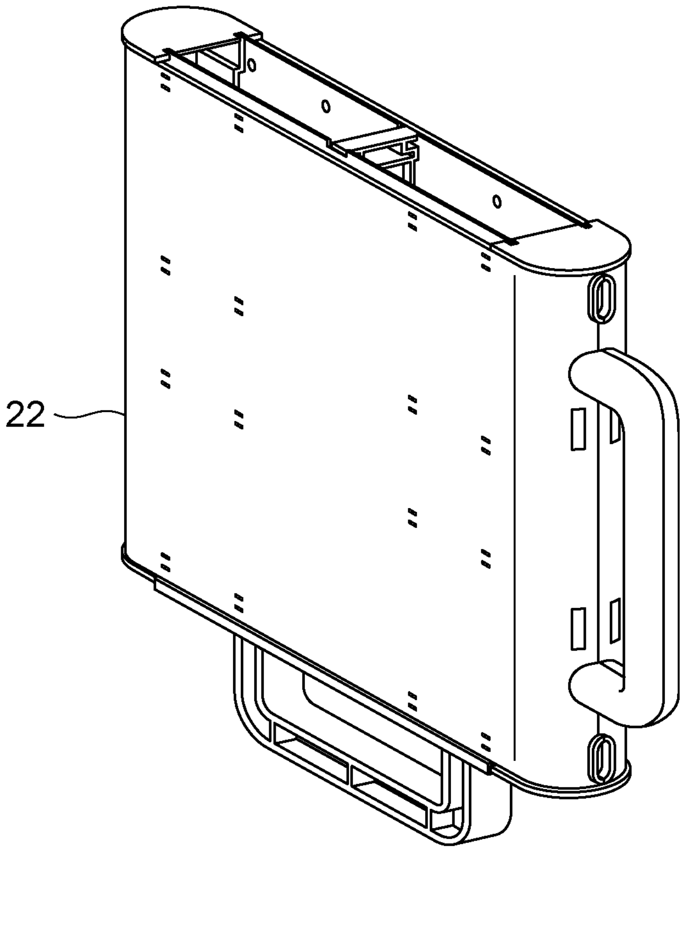
FIG. 4B is a perspective view from a bottom surface of the circuit holder in the photodynamic therapy device according to the embodiment.

FIG. 4A is a perspective view of the circuit holder 22 in the photodynamic therapy device 2 according to the embodiment, and FIG. 4B is a perspective view from a bottom surface of the circuit holder 22 in the photodynamic therapy device 2 according to the embodiment. In particular, as illustrated in FIG. 4B, the inside of the circuit holder 22 is hollow, and the circuit cooling block 6 is inserted into this hollow portion and comes into contact with the inner surface of the circuit holder 22.

Figure 4C:
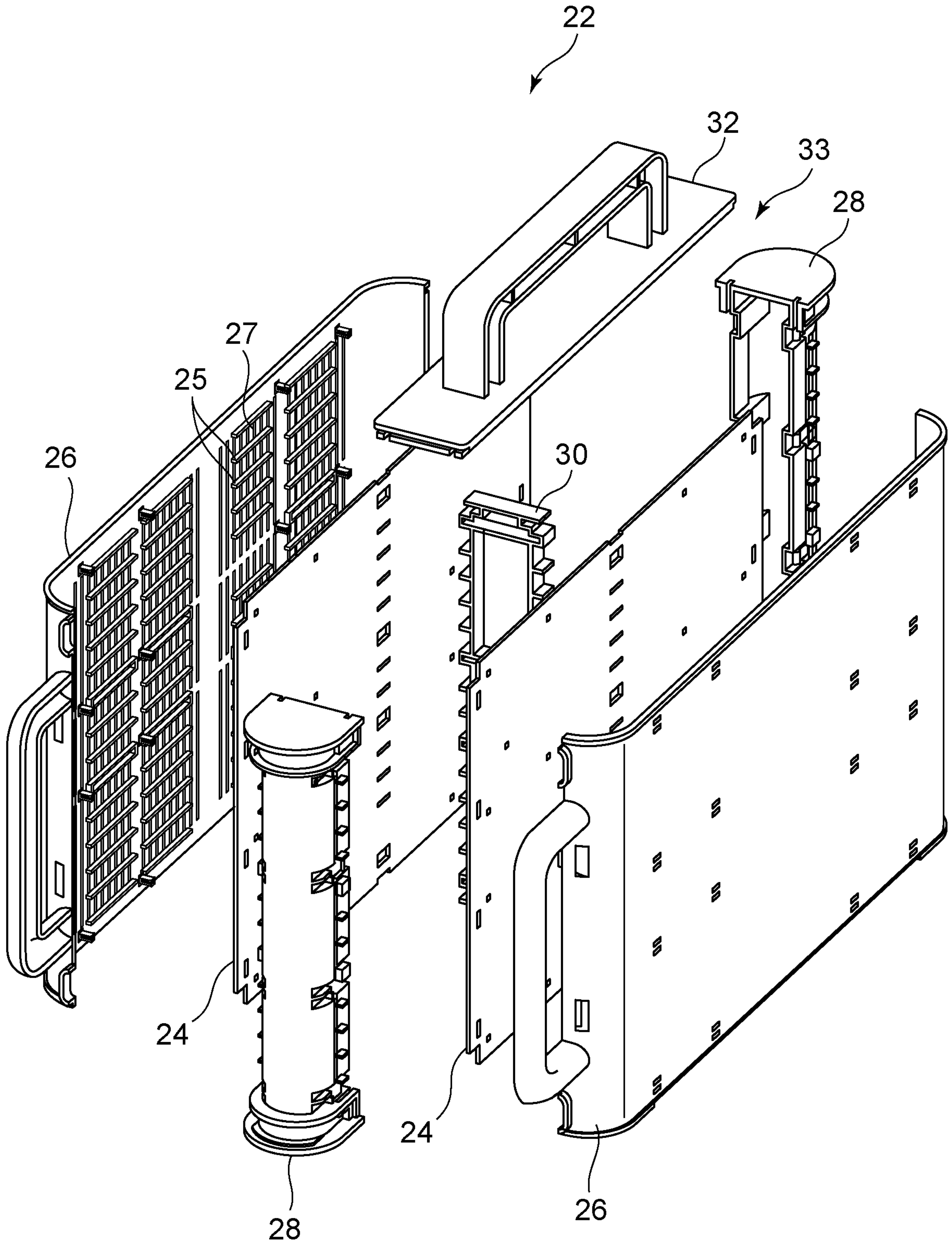
FIG. 4C is an exploded perspective view of the circuit holder in the photodynamic therapy device according to the embodiment.

FIG. 4C is an exploded perspective view of the circuit holder 22 in the photodynamic therapy device 2 according to the embodiment. As illustrated in FIG. 4C, the circuit holder 22 has a combination structure of four types of molded products and two aluminum sheet metals 24. Here, the four types of molded products are a circuit holder center portion 30, two circuit holder end portions 28, two circuit holder side surface portions 26, and a circuit holder upper surface portion 32.

Note that in the exploded view of the circuit holder 22 illustrated in FIG. 4C, the blood tube 34 connected to the blood circuit for flowing blood (that is, forming part of the blood circuit) is omitted. In the circuit holder 22, the blood tube 34 is wound around a winding core portion 33 including the two aluminum sheet metals 24, the circuit holder center portion 30, the two circuit holder end portions 28, and the circuit holder upper surface portion 32 (See FIG. 5.). A guide for winding the blood tube 34 is appropriately provided on the aluminum sheet metals 24, the circuit holder center portion 30, and the circuit holder end portions 28 so that the blood tube 34 is regularly wound around the winding core portion 33.

Each of the two circuit holder side surface portions 26 is formed of a transparent resin thin plate, for example, a polycarbonate thin plate in order to cause the irradiation light from the light source of the irradiation unit 4 to reach the blood tube 34 and the blood flowing therein. As illustrated by the circuit holder side surface portion 26 in FIG. 4C, a lateral guide 25 for winding the blood tube 34 is also appropriately provided inside the circuit holder side surface portion 26.

Furthermore, a large number of thin ribs 27 in a longitudinal direction are also provided inside the circuit holder side surface portion 26. The large number of ribs 27 in the longitudinal direction improve the adhesion of the blood tube 34 to the aluminum sheet metal 24.

Figure 5:
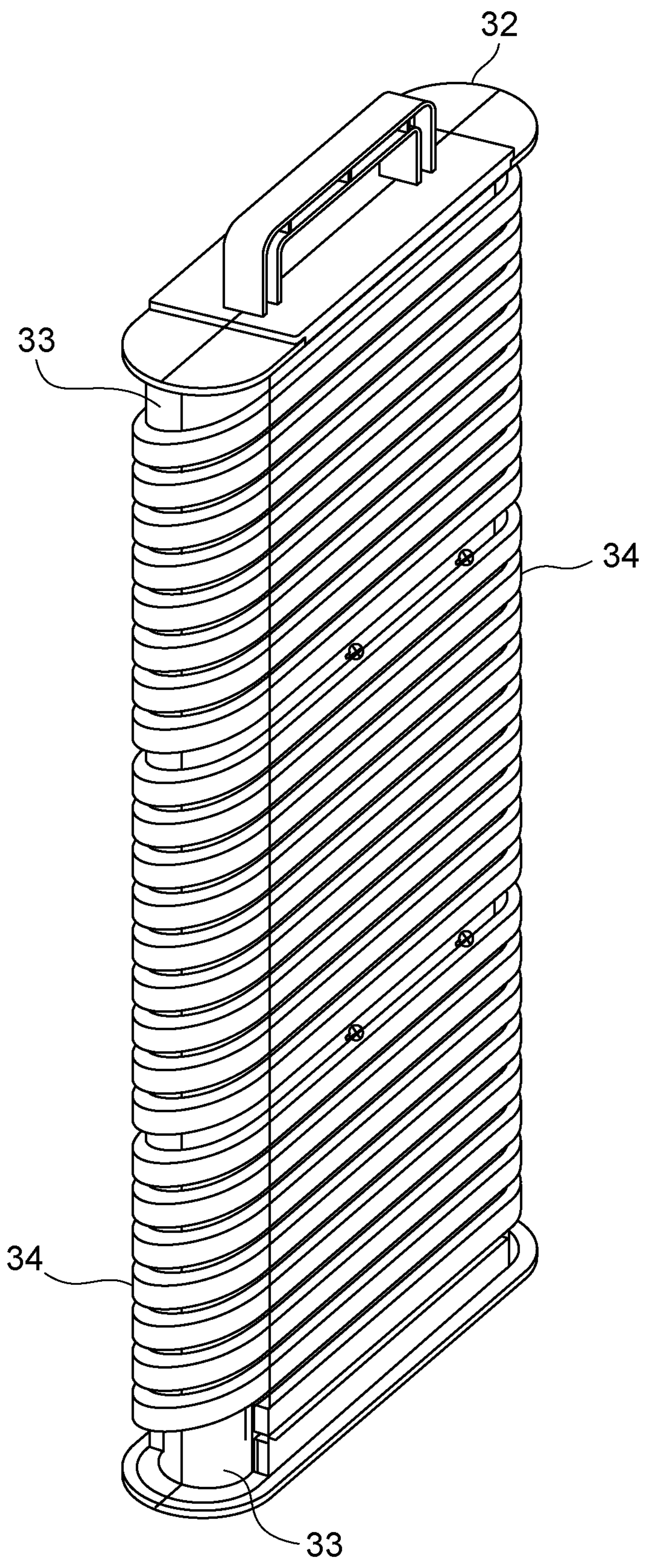
FIG. 5 is a perspective view of the photodynamic therapy device according to the embodiment in a state where a blood tube is wound around in the circuit holder.

Most of the blood tube 34 wound around the winding core portion 33 of the circuit holder 22 is sandwiched between the circuit holder side surface portion 26 that transmits the irradiation light from the light source of the irradiation unit 4 and the aluminum sheet metal 24 cooled by being in direct contact with the circuit cooling block 6. FIG. 5 is a perspective view of a state where the blood tube 34 is wound around the winding core portion 33 in the circuit holder 22 in the photodynamic therapy device 2 according to the embodiment.

Note that a transparent thin film cover may be provided between the circuit holder side surface portion 26 and the blood tube 34, or the circuit holder side surface portion 26 and the blood tube 34 may be in direct contact with each other without sandwiching anything therebetween. A cover made of a transparent thin film may also be provided between the aluminum sheet metal 24 and the blood tube 34, or the aluminum sheet metal 24 and the blood tube 34 may be in direct contact with each other without sandwiching anything therebetween.

2.1.4. Configuration of Circuit Cooling Block

Figure 6A:
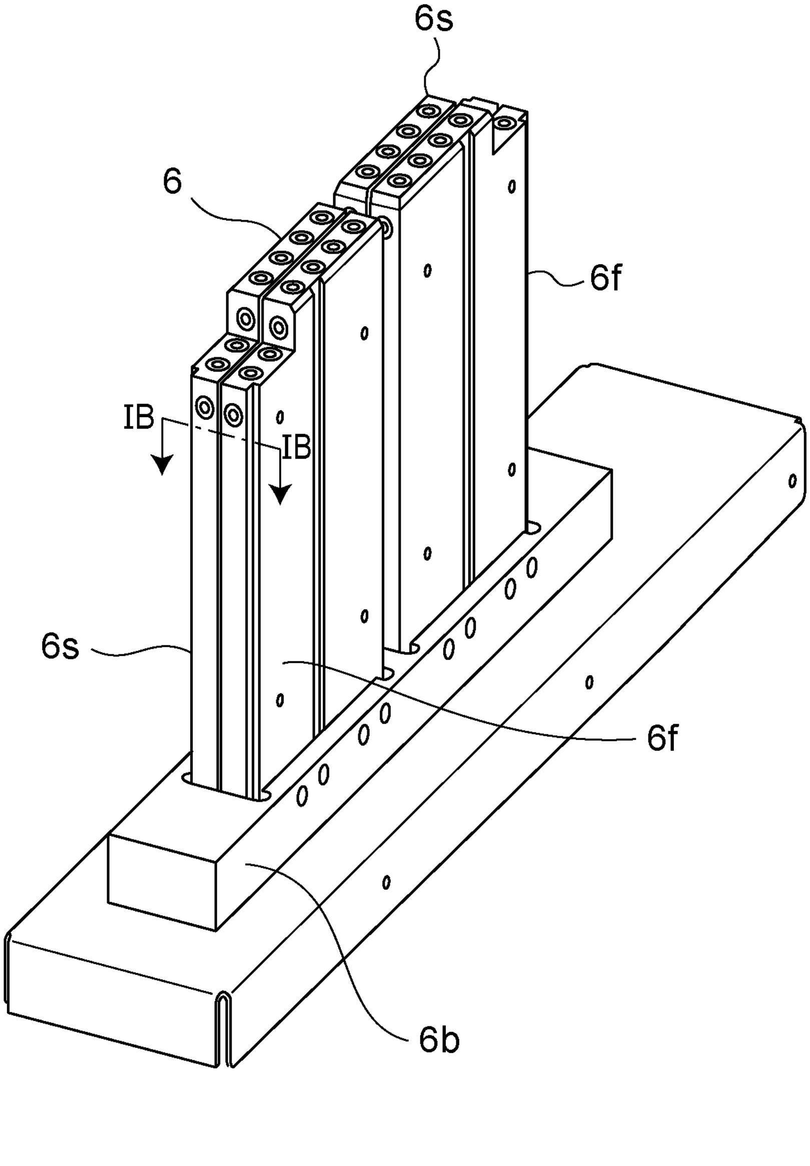
FIG. 6A is a perspective view of the circuit cooling block in the photodynamic therapy device according to the embodiment.

FIG. 6A is a perspective view of the circuit cooling block 6 in the photodynamic therapy device 2 according to the embodiment. The circuit cooling block 6 includes four circuit cooling sub-blocks (6*f*, 6*s*) and a pedestal portion 6*b* provided with the circuit cooling sub-blocks (6*f*, 6*s*). The four circuit cooling sub-blocks (6*f*, 6*s*) include two fixed circuit cooling sub-blocks 6*f* and two sliding circuit cooling sub-blocks 6*s*. The "fixed" and the "sliding" will be described later. Note that the four circuit cooling sub-blocks (6*f*, 6*s*) may have substantially the same structure. Further, the circuit cooling sub-blocks (6*f*, 6*s*) are desirably made of aluminum. Furthermore, the number of circuit cooling sub-blocks (6*f*, 6*s*) may be more than four.

Figure 7:
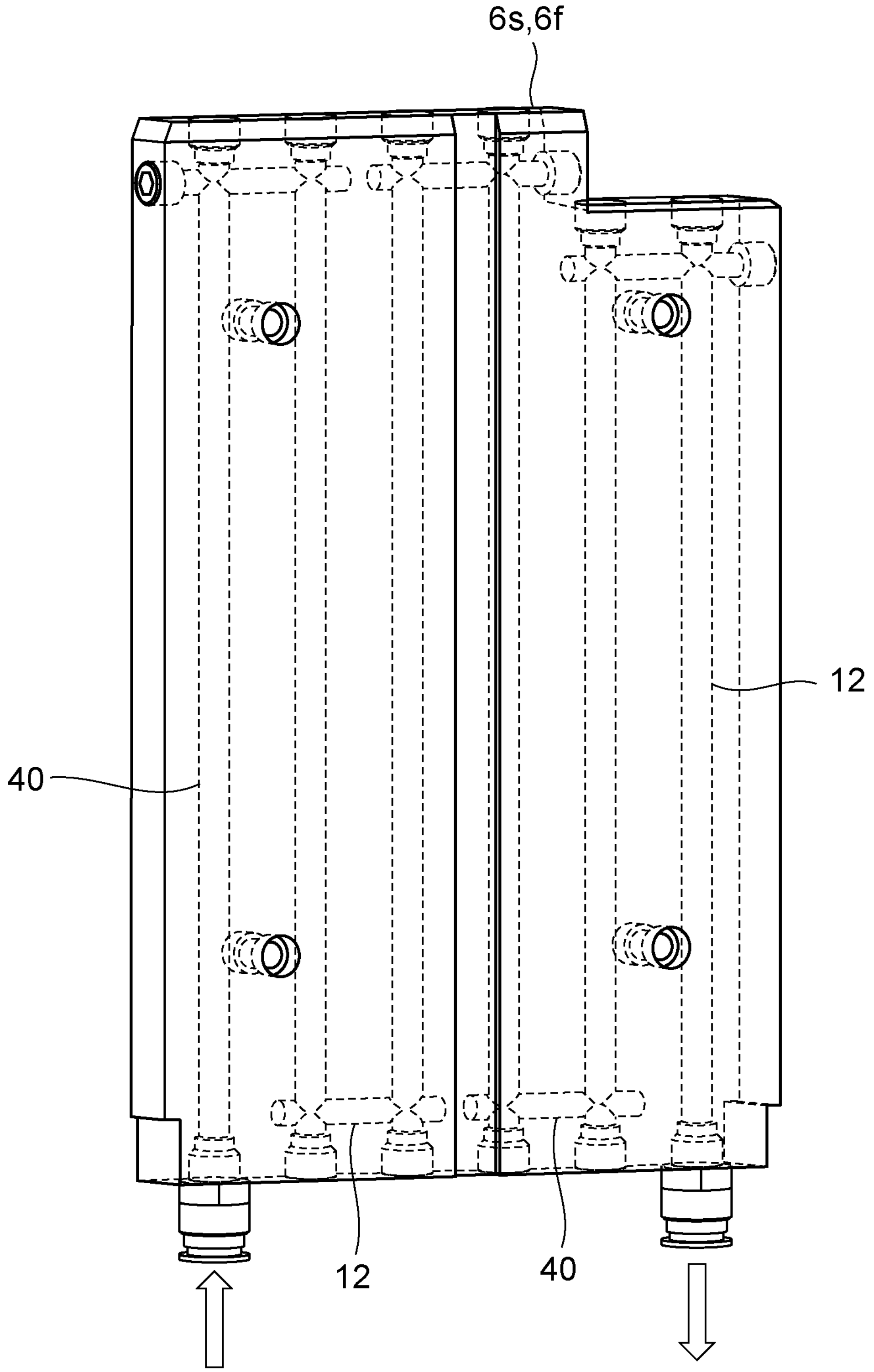
FIG. 7 is a perspective view of a circuit cooling sub-block constituting the circuit cooling block in the photodynamic therapy device according to the embodiment, and illustrates a tube through which cooling water flows.

FIG. 7 is a perspective view of the circuit cooling sub-blocks (6*f*, 6*s*) constituting the circuit cooling block 6 in the photodynamic therapy device 2 according to the embodiment, and illustrates tubes 40 through which cooling water flows. The cooling water flows in from the pedestal portion 6*b*, flows in the tubes 40 vertically and horizontally provided inside the circuit cooling sub-blocks (6*f*, 6*s*), and flows out to the pedestal portion 6*b*. The tubes 40 inside the circuit cooling sub-blocks (6*f*, 6*s*) and the pedestal portion 6*b* form a part of a water flow path 12 (See FIGS. 8 and 9.) of a cooling water circulation unit to be described later.

Figure 6B:
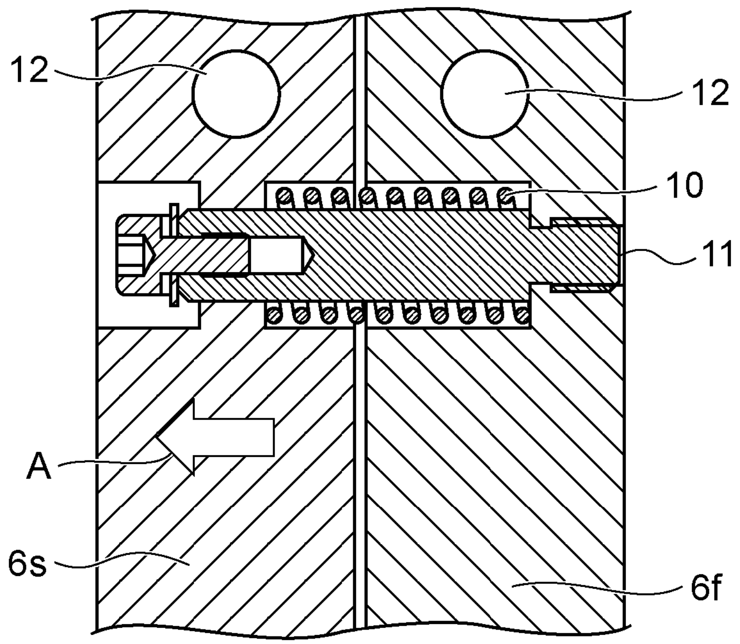
FIG. 6B is a partial cross-sectional view taken along a horizontal plane including line IB-IB in FIG. 6A in the circuit cooling block.

FIG. 6B is a partial cross-sectional view taken along a horizontal plane including line IB-IB in FIG. 6A in the circuit cooling block 6. One of the circuit cooling sub-blocks constituting the circuit cooling block 6 is of a fixed type (fixed circuit cooling sub-block 6*f*). The other of the circuit cooling sub-blocks is of a sliding type (sliding circuit cooling sub-block 6*s*). As illustrated in FIG. 6B, an elastic body 10 is sandwiched between the fixed circuit cooling sub-block 6*f* and the sliding circuit cooling sub-block 6*s* provided to face each other by being engaged with respective recesses. In the circuit cooling block 6 illustrated in FIG. 6B, a spring is used as an example of the elastic body 10.

A shaft 11 passes through the elastic body 10. This shaft 11 is configured to be fixed relative to the sliding circuit cooling sub-block 6*s* and slidable relative to the fixed circuit cooling sub-block 6*f*. This allows the sliding circuit cooling sub-block 6*s* to slide with respect to the fixed circuit cooling sub-block 6*f* while accurately maintaining a parallel positional relationship between the fixed circuit cooling sub-block 6*f* and the sliding circuit cooling sub-block 6*s*. The shaft 11 may be configured to be fixed relative to the fixed circuit cooling sub-block 6*f* and slidable relative to the sliding circuit cooling sub-block 6*s*.

In the pair of fixed circuit cooling sub-blocks 6*f* and sliding circuit cooling sub-blocks 6*s* facing each other, a plurality of the elastic bodies 10, for example, four elastic bodies are provided.

As described above, by setting the plurality of elastic bodies 10 to be sandwiched, the sliding circuit cooling sub-block 6*s* is biased in a direction of an arrow A illustrated in FIG. 6B, that is, in an outward direction. Since the sliding circuit cooling sub-block 6*s* is biased outward by the elastic bodies 10, when the circuit cooling block 6 is inserted into the circuit holder 22, the circuit cooling sub-blocks (6*s*, 6*f*) come into stronger contact with the inner surface of the aluminum sheet metal 24 of the circuit holder 22.

That is, in the two circuit cooling sub-blocks (6*s*, 6*f*) facing each other, one is fixed, and the other is held in a state where a reaction force is applied in a facing direction by the elastic body mechanism. This is to improve the adhesion of the circuit cooling sub-blocks (6*s*, 6*f*) to the aluminum sheet metal 24 of the circuit holder 22. This enhances the cooling action of the circuit cooling block 6 on the aluminum sheet metal 24 of the circuit holder 22, the blood tube 34, and thus the blood in the blood tube 34.

That is, the temperature of the blood is transferred and heat-exchanged with the blood tube 34→the aluminum sheet metal 24→the circuit cooling block 6, so that the increase in the blood temperature is suppressed.

Note that the circuit cooling block 6 may be configured such that, in the two circuit cooling sub-blocks facing each other, both are the sliding circuit cooling sub-blocks 6*s*, and the sliding circuit cooling sub-blocks 6*s* are biased outward by the elastic mechanism.

2.1.5. Configuration of Cooling Water Circulation Unit

Figure 8:
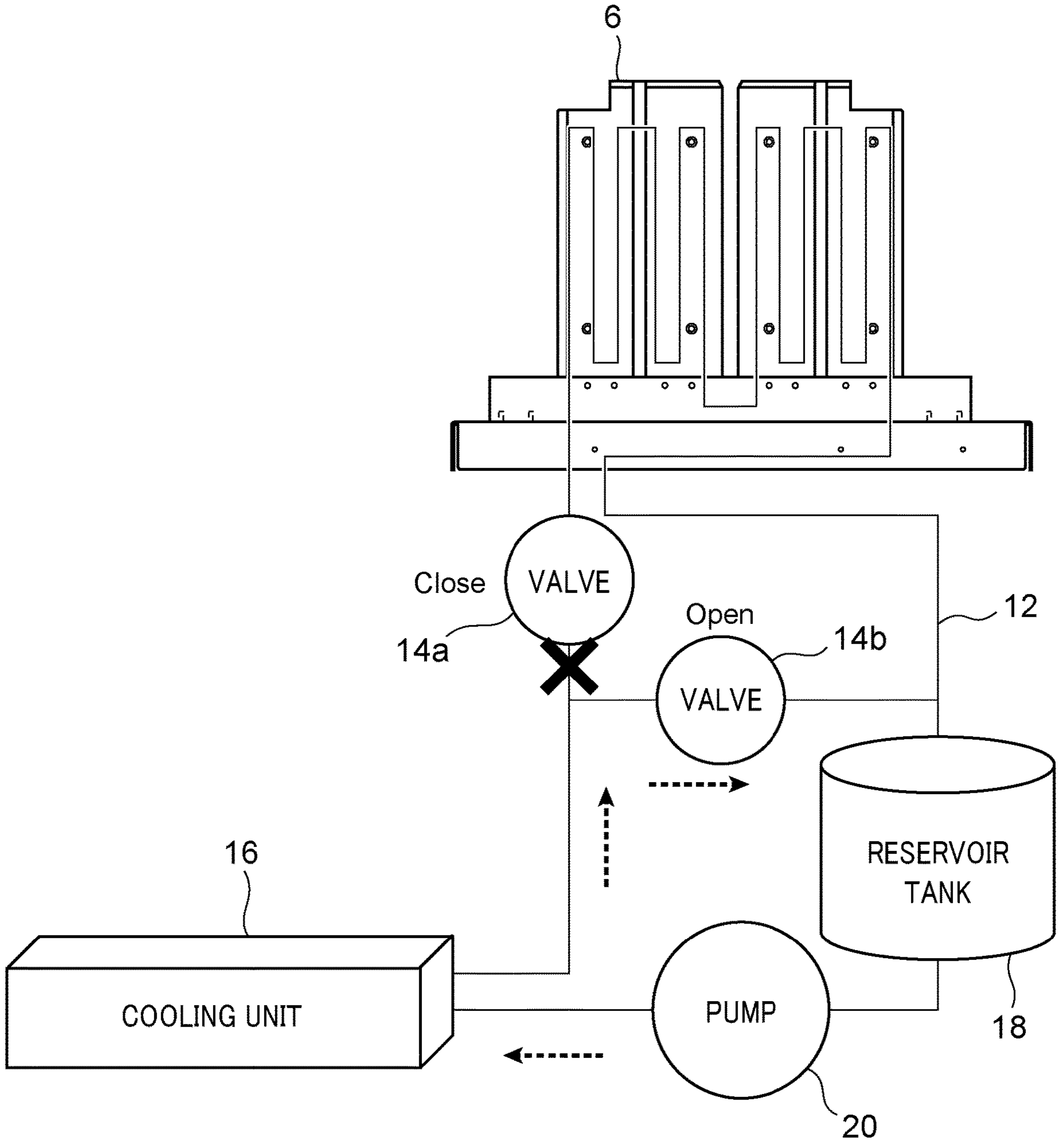
FIG. 8 is a schematic diagram of a cooling water circulation unit connected to the photodynamic therapy device according to the embodiment, and the cooling water circulation unit in the drawing is in a state at the time of preparation for treatment.
Figure 9:
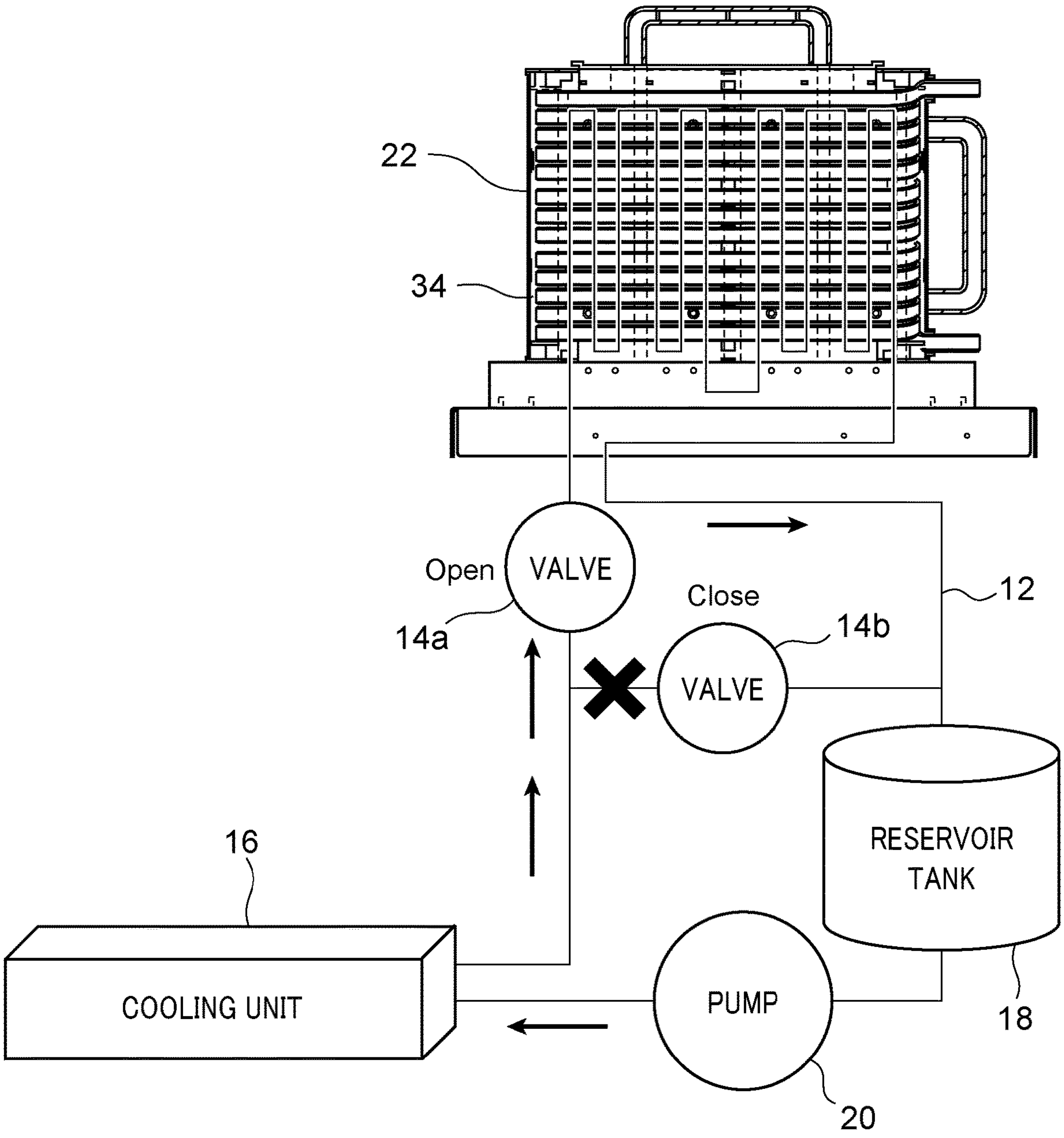
FIG. 9 is a schematic diagram of the cooling water circulation unit connected to the photodynamic therapy device according to the embodiment, and the cooling water circulation unit in the drawing is in a state at the time of treatment.

FIGS. 8 and 9 are schematic diagrams illustrating configurations of the circuit holder 22, which are accompanied by the blood tube 34 connected to the blood circuit for flowing blood (, that is, forming part of the blood circuit), the circuit cooling block 6, and the cooling water circulation unit. The cooling water circulation unit in FIG. 8 is in a state at the time of preparation for treatment. The cooling water circulation unit in FIG. 9 is in a state at the time of treatment.

As illustrated in FIGS. 8 and 9, the cooling water circulation unit includes a cooling unit 16, a first valve 14*a* and a second valve 14*b*, a reservoir tank 18, and a pump 20. The cooling unit 16, the first valve 14*a*, the circuit cooling block 6, the second valve 14*b*, the reservoir tank 18, and the pump 20 are connected by the water flow path 12 through which cooling water flows.

(In FIGS. 8 and 9, for the sake of convenience of drawing and presentation, the water flow path is illustrated in the foreground, and however,) the water flow path 12 is also provided vertically and horizontally inside the circuit cooling block 6 (See FIG. 7.). The first valve 14*a* is provided on an upstream side of the circuit cooling block 6 between the cooling unit 16 and the circuit cooling block 6. The second valve 14*b* is provided on an upstream side of the reservoir tank 18 between the cooling unit 16 and the reservoir tank 18.

As illustrated in FIG. 8, at the time of preparation for treatment, the first valve 14*a* is closed and the second valve 14*b* is opened, and cooling water is short-circuited in the cooling unit 16, the reservoir tank 18, and the pump 20, and does not flow to the circuit cooling block 6. On the other hand, as illustrated in FIG. 9, at the time of treatment, the first valve 14*a* is opened and the second valve 14*b* is closed, and the cooling water circulates through the cooling unit 16, the circuit cooling block 6, the reservoir tank 18, and the pump 20. The opening/closing operation of the first valve 14*a* and the second valve 14*b* is performed in accordance with an operation on the operation unit 5.

The cooling unit 16 is configured to cool the water circulating to the circuit cooling block 6. The cooling unit 16 includes, for example, a Peltier element. The cooling unit 16 may include a heat exchanger that cools water, and may include, for example, a radiator. Furthermore, the cooling unit 16 may be a refrigerator such as a circulating constant-temperature water tank by a compressor using a chlorofluorocarbon gas as a refrigerant. In this case, the cooling unit 16, the reservoir tank 18, and the pump 20 may be provided in a casing different from the photodynamic therapy device 2 including the circuit cooling block 6 and the irradiation unit 4. Note that in order to suppress freezing, an antifreeze liquid may be used as the cooling water.

In the present embodiment, the cooling unit 16, the first valve 14*a* and the second valve 14*b*, the reservoir tank 18, and the pump 20 constituting the cooling water circulation unit are accommodated in the lower casing 8 of the photodynamic therapy device 2 illustrated in FIGS. 1A and 1B.

2.2. Operation of Cooling Water Circulation Unit Connected to Photodynamic Therapy Device Next, an operation of the cooling water circulation unit connected to the photodynamic therapy device according to the embodiment will be described.

Referring again to FIG. 8, the cooling water circulation unit illustrated in FIG. 8 is in a state at the time of preparation for treatment. At the time of preparation for treatment, the first valve 14*a* is closed and the second valve 14*b* is opened by the operation on the operation unit 5. The cooling water is short-circuited in the cooling unit 16, the reservoir tank 18, and the pump 20, and does not flow to the circuit cooling block 6.

As described above, during the preparation for treatment, the cooling water is not circulated into the circuit cooling block 6, and is short-circuited in the cooling unit 16, the reservoir tank 18, and the pump 20, whereby the cooling water is cooled to a target temperature.

This has mainly two purposes. One is to avoid sending the cooled saline solution into the patient's body immediately after the start of treatment. That is, before starting the treatment, the blood circuit is initially filled with physiological saline. At this time, when the circuit holder 22 including the blood circuit is installed on the circuit cooling block 6 that has been sufficiently cooled, the temperature of the physiological saline in the blood circuit is further lowered by the circuit cooling block 6 without being raised by the irradiation light. It is required that this lowered temperature saline should be prevented from being fed into the body of the patient.

Another purpose is to efficiently cool the water at the time of preparation for treatment by short-circuiting.

Subsequently, referring to FIG. 9 again, the cooling water circulation unit illustrated in FIG. 9 is in a state at the time of treatment. At the time of treatment, the first valve 14*a* is opened and the second valve 14*b* is closed by the operation on the operation unit 5. The cooling water circulates through the cooling unit 16, the circuit cooling block 6, the reservoir tank 18, and the pump 20. As a result, the blood temperature rise caused by the heat generation of the blood due to the absorption of the irradiation light is suppressed.

2.3. Summary

The photodynamic therapy device 2 according to the present embodiment is a photodynamic therapy device that irradiates light from a light source onto blood that has been taken out of a patient's body and is flowing in the blood tube 34, the blood having absorbed a photoreactive agent, to destroy an undesirable component in the blood or affect the component. The photodynamic therapy device 2 includes the irradiation unit 4 that includes a light source and irradiates the blood in the blood tube 34 with light, and the circuit cooling block 6 that cools the blood in the blood tube 34. The circuit cooling block 6 is connected to the pump 20 that circulates cooling water in the circuit cooling block 6, the reservoir tank 18, and the cooling unit 16 that cools water by the water flow path 12 for flowing the cooling water.

By configuring the photodynamic therapy device 2 in this manner, in the photodynamic therapy, the temperature rise caused by the heat generation of the blood due to the absorption of the irradiation light is suppressed.

3. Other Embodiments

As described above, the embodiment has been described as an example of the technique disclosed in the present application. However, the technique in the present disclosure is not limited thereto, and can also be applied to embodiments in which changes, replacements, additions, omissions, and the like are made as appropriate.

As described above, the temperature of the blood that can be increased by the irradiation unit 4 is required to be suppressed to 40° C. or lower. Therefore, for example, in the blood circuit, a temperature sensor that detects the temperature of the blood inside the blood tube 34 immediately before returning to the circulatory organ of the patient in real time may be provided, and a controller that controls the cooling capacity of the cooling unit 16 based on a detection value of the temperature sensor may be further provided. That is, when the temperature sensor detects a temperature close to 40° C. (for example, 39° C.), the controller that has received the detection value may increase a current and/or voltage flowing through the Peltier element of the cooling unit 16 to further increase the cooling capacity. Furthermore, when the temperature sensor detects a temperature lower than a normal body temperature (for example, 34° C.), the controller that has received the detection value may be configured to decrease the current and/or voltage flowing through the Peltier element of the cooling unit 16 to further decrease the cooling capacity.

Furthermore, the accompanying drawings and the detailed description have been provided in order to describe the embodiments. Therefore, the components illustrated in the accompanying drawings and described in the detailed description not only include components essential for solving the problem but also can include, to exemplify the techniques, components that are not essential for solving the problem. For this reason, it should not be immediately recognized that those unnecessary components are necessary only because those unnecessary components are described in the accompanying drawings or the detailed description.

Furthermore, since the above-described embodiments are intended to illustrate the technique in the present disclosure, various changes, replacements, additions, omissions, and the like can be made within the scope of the claims or equivalents thereof.

REFERENCE NUMERALS

2 photodynamic therapy device
4 irradiation unit
6 circuit cooling block
6*b* pedestal portion
6*f* fixed circuit cooling sub-block
6*s* sliding circuit cooling sub-block
8 lower casing
10 elastic body
11 shaft
12 water flow path
14*a* first valve
14*b* second valve
16 cooling unit
18 reservoir tank
20 pump
22 circuit holder
24 aluminum sheet metal
25 guide
26 circuit holder side surface portion
27 rib
28 circuit holder end portion
30 circuit holder center portion
32 circuit holder upper surface portion
34 blood tube
40 tube

The invention claimed is:

1. A photodynamic therapy device that irradiates light from a light source onto blood that has been taken out of a patient's body and is flowing in a blood tube, the blood having absorbed a photoreactive agent, to destroy an undesirable component in the blood or to affect the component, the photodynamic therapy device comprising:
- an irradiation unit that includes the light source and irradiates the blood in the blood tube with light;
- a circuit cooling block that cools the blood in the blood tube, and
- a circuit holder including the blood tube and a winding core portion around which the blood tube is disposed and wound,
- wherein the circuit cooling block is connected to a pump that circulates cooling water to the circuit cooling block, a reservoir tank, and a cooling unit that cools water, by a water flow path that flows the cooling water, and
- the circuit cooling block is brought into contact with an inner surface of the circuit holder to cool the blood in the blood tube.

2. The photodynamic therapy device according to claim 1, wherein the irradiation unit is configured to be relatively movable with respect to the circuit holder and the circuit cooling block.

3. The photodynamic therapy device according to claim 1, further comprising:

a first valve provided on an upstream side of the circuit cooling block between the cooling unit and the circuit cooling block; and a second valve provided on an upstream side of the reservoir tank between the cooling unit and the reservoir tank, wherein the photodynamic therapy device is configured to short-circuit water in the cooling unit, the reservoir tank, and the pump by closing the first valve and opening the second valve when preparing for treatment.

4. The photodynamic therapy device according to claim 3, wherein the cooling unit, the circuit cooling block, the reservoir tank, and the pump are configured to circulate water, during treatment, by opening the first valve and closing the second valve.

5. The photodynamic therapy device according to claim 1, wherein the circuit cooling block includes a plurality of circuit cooling sub-blocks, one or more elastic bodies are sandwiched between a pair of the circuit cooling sub-blocks provided facing each other, and the circuit cooling block is configured to come into stronger contact with the inner surface of the circuit holder by being biased by the one or more elastic bodies.

* * * * *